United States Patent
Björk et al.

[11] Patent Number: 5,883,129
[45] Date of Patent: Mar. 16, 1999

[54] HYDROXYLATED ANTHRANILIC ACID DERIVATIVES

[75] Inventors: Susanna Karin Maria Björk, Södertälje; Birgitta Kristina Gotthammar, Stockholm; Mats Torbjörn Linderberg, Södertälje; Johan Per Luthman, Gnesta; Kerstin Margareta Irma Persson, Nykvarn, all of Sweden; Robert Schwarcz, Baltimore, Md.; Barry K. Carpenter, New York, N.Y.

[73] Assignee: Astra Aktiebolag, Sodertalje, Sweden

[21] Appl. No.: 433,337

[22] PCT Filed: Feb. 24, 1995

[86] PCT No.: PCT/SE94/00153

§ 371 Date: May 4, 1995

§ 102(e) Date: May 4, 1995

[87] PCT Pub. No.: WO94/19316

PCT Pub. Date: Sep. 1, 1994

[30] Foreign Application Priority Data

Feb. 26, 1993  [SE]  Sweden ................... 9300658

[51] Int. Cl.$^6$ .......... A61K 31/19; A61K 31/24; C07C 229/00; C07C 229/52
[52] U.S. Cl. .......... 514/56; 514/535; 562/433; 562/405; 562/452; 560/19; 560/45
[58] Field of Search .................. 562/405, 452; 514/568, 535; 560/19, 45

[56] References Cited

U.S. PATENT DOCUMENTS

| | | | |
|---|---|---|---|
| 1,847,518 | 3/1932 | Laska et al. | 562/453 |
| 2,652,332 | 9/1953 | Olcott et al. | 514/568 |
| 2,843,599 | 7/1958 | Bienert et al. | 562/453 |
| 2,894,984 | 7/1959 | Hauptschein | 562/453 |
| 3,211,610 | 10/1965 | Rogers et al. | 514/568 |
| 3,657,436 | 4/1972 | Berger et al. | 562/453 |
| 4,119,609 | 10/1978 | Allen et al. | 562/453 |
| 4,260,558 | 4/1981 | Pfister | 562/453 |
| 4,921,875 | 5/1990 | Englert et al. | 514/567 |
| 5,025,036 | 6/1991 | Carson et al. | 514/568 |
| 5,512,596 | 4/1996 | Kim et al. | 514/568 |
| 5,514,676 | 5/1996 | Ulrich et al. | 514/231.2 |

OTHER PUBLICATIONS

Preparative Biochemistry, vol. 19, No. 2, 1989, William P. Todd et al., "Preparation of 4–Halo–3–Hydroxyanthranilates and Demonstration of Their Inhibition of 3–Hydroxyanthranilate Oxygenase Activity in Rate and Human Brain Tissue", —155–165.

Wolfgang Prinz, et al., Chemical Abstracts No. 89:197117k; vol. 89, (1978), p. 590.

*Primary Examiner*—Deborah C. Lambkin
*Attorney, Agent, or Firm*—White & Case L.L.P.

[57] ABSTRACT

The present invention relates to novel derivatives of 3-hydroxyanthranilic acid, 3-HANA, of the general formula I

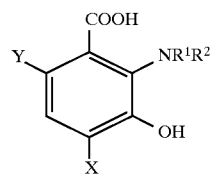

wherein $R^1$ and $R^2$ are the same or different and selected from H and alkyl; X and Y are the same or different and selected from alkoxy, aryloxy, alkyl, alkylthio, arylthio, fluoroalkyl, halogen, cyano, $OCF_3$ and $SCF_3$ with the proviso that the compound of formula I wherein $R_1$ and $R^2$=H, X=Br and Y=Me is excluded;

or a pharmaceutically acceptable salt thereof, methods and intermediates for their preparation, novel pharmaceutical compositions and the use thereof for inhibiting the enzyme 3-hydroxyanthranilate oxygenase, 3-HAO, responsible for the production of the endogenous neurotoxin quinolinic acid, QUIN.

11 Claims, No Drawings

HYDROXYLATED ANTHRANILIC ACID DERIVATIVES

This application is a 371 of PCT/SE94/00153 Feb. 24, 1995.

FIELD OF INVENTION

The present invention relates to novel derivatives of 3-hydroxyanthranilic acid, 3-HANA, methods and intermediates for their preparation, novel pharmaceutical compositions and the use thereof for inhibiting the enzyme 3-hydroxyanthranilate oxygenase, 3-HAO, responsible for the production of the endogenous neurotoxin quinolinic acid, QUIN.

BACKGROUND OF THE INVENTION

3-HAO is the enzyme in the catabolic pathway of tryptophan responsible for the conversion of 3-hydroxyanthranilic acid into quinolinic acid. Both QUIN and its biosynthetic enzyme 3-HAO have been identified in rodent as well as in human brain tissue. QUIN is an excitatory amino-acid acting through the N-methyl-D-aspartate (NMDA) receptor and has recently gained attention for its putative role as an endogenuos excitotoxin involved in neurodegenerative disorders such as Huntington's disease, stroke/cerebral ischemia, hypoxia, Alzheimers disease and the Aids dementia complex as well as epilepsi. Inhibitors of 3-HAO activity are of obvious therapeutic interest in diseases which can be traced to an overabundance of quinolinic acid.

PRIOR ART

4-Halogenated substrate analogs have been described as inhibitors of 3-HAO activity. In 1980 it was shown by Parli C J, Krieter P, Schmedt B, in "Metabolism of 6-chlorotryptophan to 4-chloroanthranilic acid: A potent inhibitor of 3-hydroxyanthranilic acid oxidase", Arch Biochem and Biophys 203, pp 161–166, 1980, that 4-chloro-3-hydroxyanthranilic acid, a metabolite of 6-chlorotryptophan, is a potent inhibitor of 3-HAO in rat and pig liver and kidney. Later it was verified by Heyes M P, Hutto B, Markey S P, in "4-Chloro-3-hydroxyanthranilate inhibits brain 3-hydroxyanthranilate oxidase", Neurochem Int 13, pp 405–408, 1988, that 4-chloro-3-hydroxyanthranilic acid also is an inhibitor of rat brain 3-HAO. In 1989 Todd W P, Carpenter B K and Schwarcz R, in "Preparation of 4-halo-3-hydroxyanthranilates and demonstration of their inhibition of 3-hydroxyanthranilate oxygenase activity in rat and human brain tissue," Prep Biochem 19, pp 155–165, 1989, showed that 4-fluoro-, 4-chloro- and 4-bromo-3-hydroxyanthranilic acid had very similar blocking potencies of 3-HAO in rat as well as in human brain.

BRIEF DESCRIPTION OF INVENTION

The present invention relates to compounds able to inhibit the enzyme 3-HAO with $IC_{50}$ values similar to and in addition a stability superior to compounds according to the prior art.

The present invention, thus is related to a compound of the general formula I

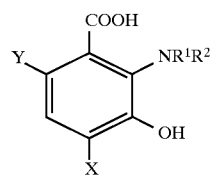

wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ with the proviso that the compound of formula I wherein $R^1$ and $R^2$=H, X=Br and Y=Me is excluded; or a pharmaceutically acceptable salt thereof.

Another object of the invention is a process for the preparation of the compound of formula I by A) in the case where $R^1$ and $R^2$=H; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$
reducing a compound of formula II

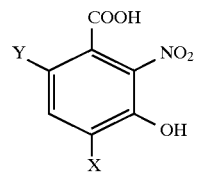

wherein X and Y are as defined in A) above;

B) in the case where $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$
deprotecting a compound of formula III

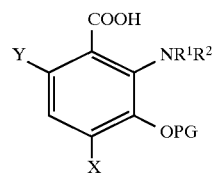

wherein $R^1$, $R^2$, X and Y are as defined in B) above and PG is a protecting group such as alkyl, benzyl (Bn), 2-(trimethylsilyl)ethoxymethyl (SEM), methoxymethyl (MOM) or 2-methoxyethoxymethyl (MEM);

C) in the case where $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$
deesterifying a compound of formula IV

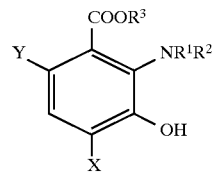

wherein $R^1$, $R^2$, X and Y are as defined in C) above and $R^3$ is selected from alkyl, Bn, SEM, MEM, MOM and 2,2,2-trichloroethyl;

D) in the case where $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ deesterifying and deprotecting a compound of formula V

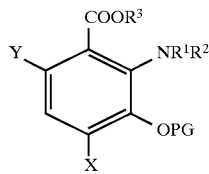

wherein $R^1$, $R^2$, X and Y are as defined in D) above nd $R^3$ and PG are selected from alkyl, Bn, SEM, MEM and MOM; or E) in the case where $R^1$=alkyl, aryl or arylalkyl $R^2$=H, alkyl, aryl or arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ alkylating a compound of formula VI

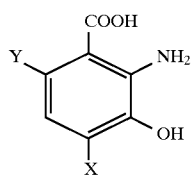

wherein X and Y are as defined in E) above.

The present invention is also related to a pharmaceutical formulation containing a compound of formula I as active ingredient and a pharmaceutically acceptable carrier, the use of said compound for the manufacture of a medicament for the prevention or treatment of neurodegeneration.

Further objects of the invention are synthesis intermediates for the preparation of compounds of formula I, namely a compound of the general formula II

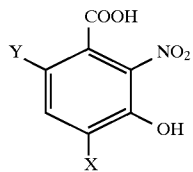

wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ with the proviso that compounds of formula II wherein X and Y=iodide; X=Br and Y=$CH_3$ are excluded;

a compound of the general formula III

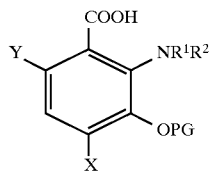

wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ and PG is a protecting group such as alkyl, Bn, SEM, MEM or MOM with the proviso that compounds of formula III where in $R^1$ and $R^2$=H, X=$OCH_3$, Y=Br, Cl or $OCH_3$ and PG=$CH_3$ are excluded;

a compound of the general formula IV

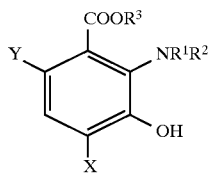

wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; and $R^3$ is selected from alkyl, Bn, SEM, MEM, MOM and 2,2,2-trichloroethyl;

a compound of the general formula V

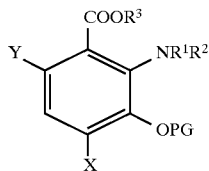

wherein $R^1$ and $R^2$ are the same or different and selected from H, alkyl, aryl and arylalkyl; X and Y are the same or different and selected from alkoxy, aryloxy, alkyl, alkylthio, arylchio, fluoroalkyl, halogen, cyano, $OSO_2CH_3$, $OSO_2CF_3$, $OCF_3$ and $SCF_3$; $R^3$ and PG are selected from alkyl, Bn, SEM, MEM and MOM with the proviso that compound of formula V wherein $R^1$ and $R^2$=H, X=$OCH_3$, Y=Cl, PG and $R^3$=$CH_3$ is excluded; and a compound of the general formula VI

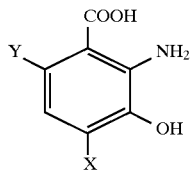

wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ with the proviso that compound of formula VI wherein X=Br and Y=$CH_3$ is excluded.

DETAILED DESCRIPTION OF THE INVENTION

The following definitions shall apply throughout the specification and the appended claims.

Unless otherwise stated or indicated, the term "alkyl" denotes a straight or branched lower alkyl group, preferably a $C_1$–$C_6$ alkyl. Examples of said lower alkyl include methyl, ethyl, n-propyl, iso-propyl, n-butyl, iso-butyl, sec-butyl, t-butyl and straight- and branched-chain pentyl and hexyl.

Unless otherwise stated or indicated, the term "aryl" denotes a phenyl, naphthyl, furyl, thienyl, pyridyl or pyrrolyl group, itself optionally substituted.

Unless otherwise stated or indicated, the term "aryl-alkyl" denotes a lower alkyl group as defined above substituted by an aryl group as defined above. Examples of said arylalkyl include benzyl, phenethyl, phenylpropyl, phenylbutyl, 2,4-dimethoxyphenylmethyl, furfuryl, 3-furylmethyl, tolylethyl and thenyl.

Unless otherwise stated or indicated, the term "alkoxyl" denotes a straight or branched lower alkoxy group, preferably a $C_1$–$C_6$ alkoxy. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term "alkylthio" denotes a straight or branched lower alkylthio preferably a $C_1$–$C_6$ alkylthio. Examples of said lower alkylthio include methylthio, ethylthio, n-propylthio, iso-propylthio, n-butylthio, iso-butylthio, sec-butylthio, t-butylthio and straight- and branched-chain pentylthio and hexylthio.

Unless otherwise stated or indicated, the term "aryuthino" denotes a phenylthio group in which the phenyl ring is optionally further substituted by lower alkyl lower alkoxy or halogen.

Unless otherwise stated or indicated, the term "aryloxy" denotes a phenoxy group in which the phenyl ring is optionally further substituted by lower alkyl, lower alkoxy or halogen.

Unless otherwise stated or indicated, the term "halogen" shall mean fluorine, chlorine, bromine or iodine.

The best mode o f carrying out the invention known at present is to use 4,6-dibromo-3-hydroxyanthranilic acid or 4,6-dichloro-3-hydroxyanthranilic acid.

The compounds according to the present invention may be used in connection with prevention or treatment of neurodegeneration, especially in connection with conditions such as stroke, cerebral ischaemia, hypoxia, epilepsy and in neurodegenerative diseases such as Alzheimer's disease, multi-infarct dementia, Huntington's disease and the AIDS dementia complex.

Below the methods for the preparation of the compound of formula I will be described in detail.

Methods of Preparation

The compound of formula I

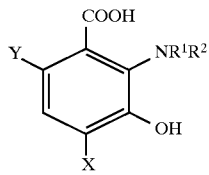

I wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ may be prepared by one of the following methods.

Method A The compound of formula I wherein $R^1$ and $R^2$ are H; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula II

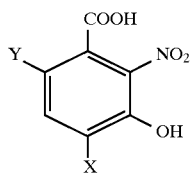

II wherein X and Y are as defined in formula I in method A, by reduction with for example $H_2$ and a catalyst such as Pd/C, Raney nickel or $PtS_2$ at atmospheric or elevated pressure in a suitable solvent such as EtOH or EtOAc. The reduction can also be accomplished by reaction with $SnCl_2$, $NH_2NH_2.H_2O$ or $Na_2S_2O_5$ in a suitable solvent such as EtOH.

Method B The compounds of the general formula I wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of the general formula III

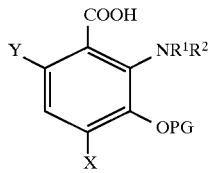

III wherein $R^1$, $R^2$, X and Y are as defined in formula I in method B and PG is selected from alkyl, Bn, SAM, MEM and MOM, by deprotection with for example a Lewis acid such as $BBr_3$ or trimethylsilyl iodide or with alkyl- or arylSNa or alkyl- or arylSLi followed by adjustment of the pH to obtain the 3-hydroxyanthranilic acid derivative. In the case where PG=SEM, deprotection can be performed using tetrabutylammonium fluoride (TBAF) or CsF in a suitable solvent such as N,N-dimethylpropylenurea (DMPU) or N,N-dimethylformamide (DMF) at elevated temperature. A benzyl group can be removed by hydrogenolysis using for example $H_2$ and Pd/C or $PtS_2$ as a catalyst. A 2,2,2-trichloroethyl group can be removed using Zn in acetic acid.

Method C The compounds of formula I wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula IV

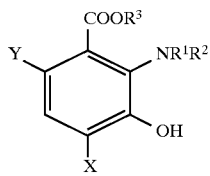

IV wherein $R^1$, $R^2$, X and Y are as defined in formula I in method C and $R^3$ is selected from alkyl, Bn, SEM, MEM, MOM and 2,2,2-trichloroethyl, by deesterifying with for example a base such as KOH in a suitable solvent such as MeOH at room temperature or at elevated temperature, or by alkyl- or arylSLi or alkyl- or arylSNa or with $Me_3SiI$ followed by adjustment of the pH to obtain the 3-hydroxyanthranilic acid deivative. In the case where $R^3$=Bn the carboxylic acid can be obtained by hydrogenolysis with for example $H_2$ and Pd/C or $PtS_2$. A 2,2,2-trichloroethylester can be cleaved for example with Zn in HOAc and a SEM-ester for example with TBAF in DMPU.

Method D The compounds of formula I wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula V

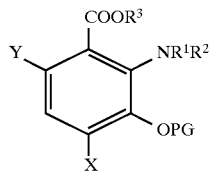

V wherein $R^1$, $R^2$, X and Y are as defined in formula I in method D; PG and $R^3$ are selected from alkyl, Bn, SEM, MEM and MOM, by deesterification and deprotection with for example alkyl- or arylSLi, alkyl- or arylSNa or with $Me_3SiI$ followed by adjustment of the pH to obtain the 3-hydroxyanthranilic acid derivative. In the case where PG and $R^3$=Bn the 3-hydroxyanthranilic acid derivative can be obtained by hydrogenolysis for example with $H_2$ and Pd/C or $PtS_2$ and if PG and $R^3$=SEM, TBAF can be used.

Method E The compound of formula I wherein $R^1$=alkyl, aryl or arylalkyl; $R^2$=H, alkyl, aryl or arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula VI

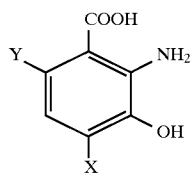

VI wherein X and Y are as defined in formula I in method E, by reductive alkylation with for example an aldehyde corresponding to $R^1$ and a reducing agent such as $NaCNBH_3$ and HCl in a suitable solvent such as $CH_3CN$, $H_2O$ or MeOH. Mono- and di-N-alkylated derivatives can be separated for example by chromatography.

Intermediates

Method II:a Compounds of formula II wherein X and Y are the same or different and selected from alkoxy, alkyl, alkylthio, fluoroalkyl, halogen, cyano, $OSO_2CH_3$, $OSO_2CF_3$, $OCF_3$ and $SCF_3$; may be prepared from compounds of formula VII

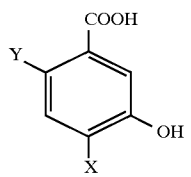

VII wherein X and Y are as defined in formula II in method II:a, by nitration using for example $HNO_3$ in a solvent such as $CH_3NO_2$, $CH_2Cl_2$ or $H_2O$ or a mixture of $HNO_3$ and $H_2SO_4$.

Method II:b Compounds of formula II wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula VIII

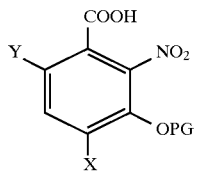

wherein X and Y are as defined in formula II in method II:b and PG is selected from alkyl, Bn, SEM, MEM and MOM, by deprotection for example according to method B.

Method II:c Compounds of formula II wherein X=Br, Cl or I; Y is selected from alkoxy, alkyl, alkylthio, fluoroalkyl, halogen, cyano, $OSO_2CH_3$, $OSO_2CF_3$, $OCF_3$ and $SCF_3$; may be prepared from compounds of formula IX

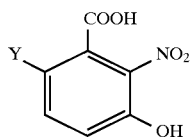

IX wherein Y is as defined in formula II in method II:c, by halogenation with for example $Br_2$ or $Cl_2$ in acetic acid at room- or elevated temperature. Alternatively, IX could be halogenated with $Br_2$ or $I_2$ and mercuric trifluoroacetate in trifluoroacetic acid at room- or elevated temperature.

Method II:d Compounds of formula II wherein X is selected from alkoxy, alkyl, alkylthio, fluoroalkyl, halogen, cyano, $OSO_2CH_3$, $OSO_2CF_3$, $OCF_3$ and $SCF_3$; Y=Br, Cl or I; may be prepared from compounds of formula X

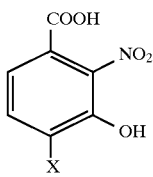

X wherein X is as defined in formula II in method II:d, by halogenation for example according to method II:c.

Method II:e Compounds of formula II wherin X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and SCF3; may be prepared from compounds of formula XI

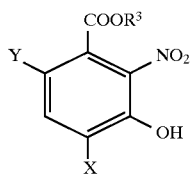

wherein X and Y are as defined in formula II in method II:e and $R^3$=alkyl, Bn, SEM, MEM, MOM or 2,2,2-trichloroethyl, by deesterification for example according to method C.

Method II:f Compounds of formula II wherein X and Y=Br, Cl or I may be prepared from compounds of formula XX

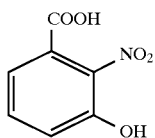

by halogenation according to method II:c.

Method III:a Compounds of formula III wherein and $R^2=H$; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ and PG is selected from alkyl, Bn, SEM, MEM and MOM; may be prepared from compounds of formula VIII

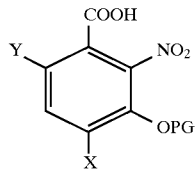

wherein X, Y and PG are as defined in formula III in method III:a, by reduction for example according to method A.

Method III:b Compounds of formula III wherein $R^1$ and $R^2=H$; X and Y are the same or different and selected from alkoxy, alkyl, alkylthio, fluoroalkyl, chloro, fluoro and $OCF_3$; PG is selected from alkyl, SEM and MOM; may be prepared from compounds of formula XII

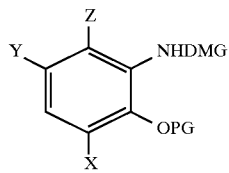

wherein X, Y and PG are as defined in formula III in method III:b; DMG is selected from COtBu, $CO_2tBu$ and $COCF_3$; Z=H or Br by reaction with for example alkyllithium in a suitable solvent such as tetrahydrofuran(THF) at low temperature. The aryllithium derivative is then reacted with $CO_2$ (s), acidified and the DMG group is removed by aqueous HCl at elevated temperature.

Method III:c Compounds of formula III wherein $R^1=H$, alkyl, aryl or arylalkyl; $R^2=H$; X and Y are the same or different and selected from alkoxy, aryloxy, alkyl, fluoroalkyl, halogen and $OSO_2CH_3$, $OSO_2CF_3$, $OCF_3$; PG is selected from alkyl, Bn, MEM and MOM; may be prepared from compounds of formula XIII

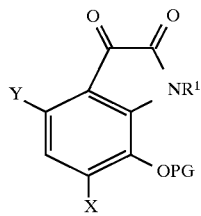

wherein X, Y, $R^1$ and PG are as defined in formula III in method III:c, by reacting a compound of formula XIII with for example $H_2O_2$ and NaOH in a suitable solvent such as water or dioxan. The pH is then adjusted to obtain the anthranilic acid derivative.

Method III:d Compounds of formula III wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; PG is selected from alkyl, Bn, SEM, MEM and MOM; may be prepared from compounds of formula V

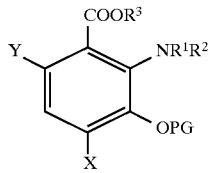

wherein $R^1$ $R^2$ X, Y and PG are as defined in formula III in method III:d and $R^3$ is selected from alkyl, Bn, SEM, MEM, MOM and 2,2,2-trichloroethyl and different from PG, by deesterification for example according to method C.

Method III:e Compounds of formula III wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, fluoro, chloro, cyano, $OSO_2CH_3$, $OCF_3$ and $SCF_3$ and PG is selected from alkyl and Bn; may be prepared from compounds of formula XVIII

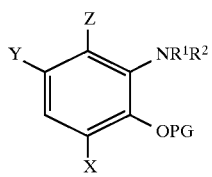

wherein $R^1$, $R^2$, X, Y and PG are as defined in formula III in method III:e and Z=$OSO_2CF_3$, I or Br, by reacting a compound of formula XVIII with for example a mixture of $Pd(OAc)_2$, CO, 1,3-bis(diphenylphosphino)-propane and water in a suitable solvent such as DMF or dioxan containing a base such as $Et_3N$.

Method IV:a Compounds of formula IV wherein $R^1$ and $R^2=H$; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; $R^3$ is selected from alkyl, Bn, SEM, MEM, MOM and 2,2,2-trichloroethyl; may be prepared from compounds of formula XI

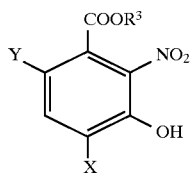

wherein X, Y and $R^3$ are as defined in formula IV in method IV:a, by reduction for example according to method A.

Method IV:b Compounds of formula IV wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; and $R^3$ is selected from akyl, Bn, SEM, MEM, MOM and 2,2,2-trichloroethyl; may be prepared from compounds of formula V

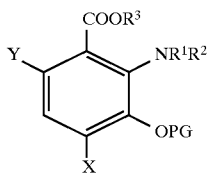

wherein $R^1$, $R^2$, X, Y and $R^3$ are as defined in formula IV in method IV:b and PG is selected from alky.l, Bn, SEM, MEM and MOM and different from $R^3$, by deprotection for example according to method B.

Method IV:c Compounds of formula IV wherein $R^1$=H, alkyl, aryl or arylalkyl; $R^2$=alkyl, aryl or arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; $R^3$ is selected from alkyl, benzyl, SEM, MEM, MOM and 2,2,2-trichloroethyl; may be prepared from compounds of formula XIV

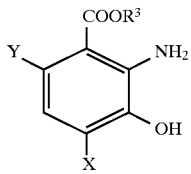

wherein X, Y and $R^3$ are as defined in formula IV in method IV:c, by alkylation for example according to method E.

Method V:a Compounds of formula V wherein $R^1$ and $R^2$=H; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; $R^3$ and PG are selected from alkyl, Bn, SEM, MEM and MOM; may be prepared from compounds of formula XV

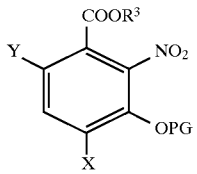

wherein X, Y, $R^3$ and PG are as defined in formula V in method V:a, by reduction for example according to method A.

Method V:b Compounds of formula V wherein $R^1$ and $R^2$=H; X and Y are the same or different and selected from alkoxy, aryloxy, alkyl, alkylthio, arylthio, fluoroalkyl, halogen, cyano, $OCF_3$ and $SCF_3$; $R^3$ and PG are selected from alkyl, Bn and SEM; may be prepared from compounds of formula XVI

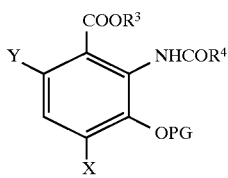

wherein X, Y, $R^3$ and PG are as defined in formula V in method V:b and $R^4$=t-Bu, t-BuO or $CF_3$, by hydrolysis with for example an acid such as HCl(aq) or $CF_3COOH$ followed by adjustment of the pH to obtain the anthranilic acid derivative.

Method V:c Compounds of formula V wherein $R^1$=H, alkyl, aryl or arylalkyl; $R^2$=alkyl, aryl or arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; $R^3$ and PG are selected from alkyl, Bn, SEM, MEM and MOM; may be prepared from compounds of formula XVII

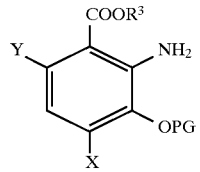

wherein X, Y, $R^3$ and PG are as defined in formula V in method V:c, by alkylation for example according to method E.

Method V:d Compounds of formula V wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, fluoro, chloro, cyano, $OSO_2CH_3$, $OCF_3$ and $SCF_3$; $R^3$ and PG are selected from alkyl and Bn; may be prepared from compounds of formula XVIII

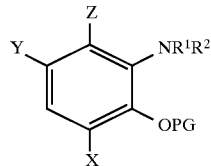

wherein $R^1$, $R_2$, X, Y and PG are as defined in formula V in method V:d and Z=$OSO_2CF_3$, I or Br, by reacting a compound of formula XVIII with for example a mixture of $Pd(OAc)_2$, CO, 1,3-bis(diphenylphosphino)-propane and an alcohol corresponding to $R_3$ in a suitable solvent such as DMF or dioxan containing a base such as $Et_3N$.

Method V:e Compounds of formula V wherein $R^1$ and $R^2$=H; X and Y are the same or different and selected from alkoxy, alkyl, alkylthio, fluoroalkyl, chloro, fluoro and $OCF_3$; PG is selected from alkyl, SEM and MOM; may be prepared from compounds of formula XII

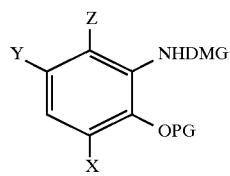

wherein X, Y and PG are as defined in formula V in method V:e; DMG=COtBu, $CO_2tBu$ or $COCF_3$; Z=H or Br, by reaction with for example alkyllithium in a suitable solvent such as THF at low temperature. The aryllithium derivative is then reacted with methyl or benzyl chloroformiate and the DMG group is removed by aqueous HCl at elevated temperature.

Method VI:a Compounds of formula VI wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula II

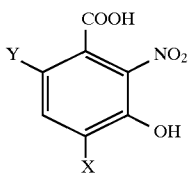

wherein X and Y are the same as defined in formula VI in method VI:a, by reduction for example according to method A.

Method VI:b Compounds of formula VI Wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula XIX

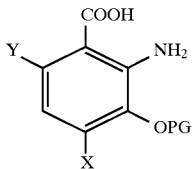

wherein X and Y are as defined in formula VI in method VI:b and PG is selected from alkyl, Bn, SEM, MEM and MOM, by deprotection for example according to method B.

Method VI:c Compounds of formula VI wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula XIV

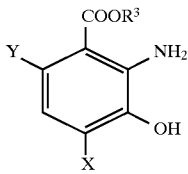

wherein X and Y are as defined in formula VI in method VI:c and $R^3$ is selected from alkyl, Bn, SEM, MEM, MOM and 2,2,2-trichloroethyl, by deesterifying for example according to method C.

Method VI:d Compounds of formula VI wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; may be prepared from compounds of formula XVII

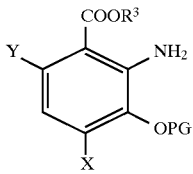

wherein X and Y are as defined in formula VI in method VI:d and $R^3$ and PG are selected from alkyl, Bn, SEM, MEM and MOM, by deesterification and deprotection for example according to method D.

WORKING EXAMPLES

Example 1 (Method A)

Preparation of 4,6-dibromo-3-hydroxyanthranilic acid 4,6-Dibromo-3-hydroxy-2-nitrobenzoic acid To a cooled, stirred mixture of 3-hydroxy-2-nitrobenzoic acid (10.47 g, 0.57 mol) and sodium acetate (9.85 g, 0.57 mol) in HOAc (100 mL), $Br_2$(6.15 mL, 0.12 mol) was added dropwise. The mixture was stirred at 60° C. for 68 h and then cooled to room temperature and the salts were filtered off. Evaporation of the filtrate gave a residue which was dissolved in $EtOAc/H_2O$ and acidified with HCl (2M). The aqueous phase was extracted with EtOAc and the combined organic layers dried ($MgSO_4$) and evaporated to give a crude product (18.9 g). Purification by flash chromatography ($SiO_2$, toluene—HOAc) followed by crystallization from MeOH gave the title compound (15.37 g). Mp: 201°–202° C. (dec.). $^1H$ NMR (DMSO-$d_6$): δ 8.20 (s, 1 H). $^{13}C$ NMR (DMSO-$d_6$): δ 164.42, 146.93, 139.10, 130.48, 116.17, 108.14. MS (EI, 70 eV): m/z (rel. int) 339, 341, 343 ($M^+$, 49, 98, 46).

4,6-Dibromo-3-hydroxyanthranilic acid 4,6-Dibromo-3-hydroxy-2-nitrobenzoic acid (4.09 g, 12 mmol) and $PtS_2$ (160 mg, 0.62 mmol) in EtOH (150 mL) was hydrogenated at atmospheric pressure and room temperature for 45 h. Filtration and evaporation of the filtrate gave a crude product (3.69 g) which was purified by flash chromatography ($SiO_2$, toluene-EtOAc). Treatment with activated charcoal in MeOH and crystallization from MeOH/$H_2O$ gave the title compound (2.51 g). Mp: 162°–164.5° C. $^1H$ NMP (DMSO-$d_6$): δ 6.96 (s, 1 H). $^{13}C$ NMR (DMSO-$d_6$): δ 167.69, 140.56, 139.95, 121.81, 117.23, 112.53, 110.45. MS(EI, 70ev): m/z (rel. int.) 309, 311, 313 ($M^+$, 36, 72, 34).

Example 2 (Method A)

Preparation of 4-bromo-3-hydroxy-6-methoxyanthranilic acid

4-Bromo-3-hydroxy-6-methoxybenzoic acid

3-Hydroxy-6-mezhoxybenzoic acid[1] (1.24 g, 7.40 mmol) was dissolved in acetic acid (100 mL) by heating to 60° C. After cooling to room temperature bromine (0.38 mL, 7.4 mmol) was added dropwise. The reaction mixture was stirred for 3 h and then evaporated under reduced pressure giving a crude product of 1.74 g. Purification by silica gel chromatography (HOAc-toluene 1:10) gave 1.5 g of the title compound. $^1H$ NMR ($CD_3OD$): δ 7.38 (s, 1 H), 7.26 (s, 1 H), 3.84 (s, 3 H). $^{13}C$ NMR ($CD_3OD$): 67 168.95, 154.07, 149.60, 121.31, 119.63, 119.02, 116.57, 57.68.

4-Bromo-3-hydroxy-6-methoxy-2-nitrobenzoic acid

Sodium nitrate (361 mg, 4.25 mmol) was dissolved in water (4 mL) and $LaNO_3*6H_2O$ (18 mg, 0.04 mmol) and HCl (12M, 4 mL) were added. The solution was cooled to 0° C. and a slurry of 4-bromo-3-hydroxy-6-methoxybenzoic acid in diethyl ether (20 mL) was added to the reaction mixture in portions during 10 min. After slowly raising the temperature to room temperature the mixture was stirred for 7 h. Extraction between $H_2O$ (20 ml) and $CH_2Cl_2$ (3×30 mL), drying the organic phase with MgSO4, filtration and evaporation under reduced pressure gave a mixture of products. Purification by silica gel chromatography (HOAc-EtOAc-toluene 1:2:8) gave the title compound (0.6 g). $^1H$ NMR ($CD_3OD$): δ 7.57 (s, 1 H), 3.85 (s, 3 H). MS (EI, 70 eV): m/z (rel.int.) 291/293 ($M^+$, 21/19).

4-Bromo-3-hydroxy-6-methoxyantranilic acid

4-Bromo-3-hydroxy-6-methoxy-2-nitrobenzoic acid (52 mg, 0.18 mmol) was dissolved in EtOH (7 mL) and $PtS_2$ (2 mg) was added. Hydrogenation at atmospheric pressure and room temperature for 18 h, filtration and then evaporation under reduced pressure gave 50 mg crude product. Purification on a silica gel column (HOAc-EtOAc-toluene, 1:2:8) gave 30 mg of the title compound (95% pure according to HPLC). $^1$H NMR (CD$_3$OD): δ 6.40 (s, 1), 3.88 (s, 3 H). $^{13}$C NMR (CD$_3$OD): δ 170.82, 154.76, 145.58, 137.80, 115.54, 102.08, 101.61, 57.62. MS (EI, 70 eV): m/z 261/263 (M$^+$, 80/79).

Example 3 (Method A)

Preparation of 6-fluoro-3-hydroxy-4-propylanthranilic acid hydrochloride

Allyl [[5-(1,1-dimethylethyl)dimethylsilyloxy]-2-fluorophenyl] ether

5-[(1,1-Dimethylethyl)dimethylsilyloxy]-2-fluorophenol$^2$ (65 g, 0.27 mol) was reacted with allyl bromide (40 mL, 0.46 mol) and K$_2$CO$_3$ (50 g, 0.36 mol) in acetone (200 mL) at reflux temperature for 6 h. Evaporation of the solvent, partition of the residue between water (500 mL) and diethyl ether (500 mL), extraction of the aqueous phase with diethyl ether (250 mL) and drying the combined organic phases (MgSO$_4$) followed by evaporation gave allyl [[5-(1,1-dimethylethyl)dimethylsilyloxy]-fluoro-phenyl] ether (75 g) as a crude product. A sample was purified by column chromatography (SiO$_2$) using EtOAc-hexane 5:95 as eluent. $^1$H NMR (CDCl$_3$): δ 6.91 (dd, J$_1$=8.8 and J$_2$=11.1 Hz, 1 H), 6.46 (dd, J$_1$=2.8 and J$_2$=7.2 Hz, 1 H), 6.37–6.32 (m, 1 H), 6.12–5.89 (m, 1 H), 5.42 (dm, J=17.1 Hz, 1 H), 5.30 (dm, J=10.5 HZ, 1 H), 4.56 (dt, J$_1$=1.6 and J$_2$=3.7 Hz, 2 H), 0.98 (s, 9 H), 0.18 (s, 6 H). MS (EI, 70 eV): m/z (rel.int.) 282 (M$^+$, 7).

Allyl (2-fluoro-5-methoxy-phenyl)ether

Allyl [[5-(1,1-dimethylethyl)dimethylsilyloxy]-2-fluorophenyl] ether(70 g, 70%, 0.17 mol), KF (28.8 g, 0.50 mol) and CH$_3$I (52.5 g, 0.37 mol) were reacted in DMF (300 mL) at room temperature for 1 h 15 min. Potassium carbonate (27.6 g, 0.20 mol) was added and the mixture was stirred overnight at room temperature, followed by 4 h at 60° C. Evaporation of the solvent gave a residue which was extracted between water and ether and the organic phase was washed with brine, dried (MgSO$_4$) and evaporated to give allyl (2-fluoro-5-methoxyphenyl)ether (42.4 g) as a crude product. A sample was purified by column chromatography (SiO$_2$) using EtOAc-Hexane 1:9 as eluent. $^1$H NMR (CDCl$_3$): δ 6.98 (dd, J$_1$=8.8 and J$_2$=11.0 Hz, 1 H), 6.53 (dd, J$_1$=2.9 and J$_2$=7.1 Hz, 1 H), 6.38 (dt J$_1$=3.0 and J$_2$=9.0 Hz, 1 H), 6.16–5.95 (m, 1 H), 5.42 (dm, J=17.1 Hz, 1 H), 5.31 (dm, J=10.4 Hz, 1 H), 4.58 (dt, J$_1$=1.5 and J$_2$=5.4 Hz, 2 H), 3.76 (s, 3 H). MS (EI, 70 eV): m/z (rel.int.) 182 (M$^+$, 84).

4-Allyl-2-fluoro-5-methoxyphenol

Allyl (2-fluoro-5-methoxyphenyl)ether (32.4 g, 60%, 0.11 mol) was dissolved in ethylene glycol (150 mL) and heated to 160° C. for 16 h. Water (1 L) and 2M HCl (100 mL) were added followed by extraction with ether (500+2×250 mL). The combined organic phases were extracted with 0.7M NaOH (500+250 mL). The aqueous phase was acidified with 2M HCl (350 ml) and extracted with ether (3×250 ml) and the organic phase was washed with brine (100 ml), dried (MgSO$_4$) and concentrated giving 24.5 g of crude product. Purification by column chromatography (SiO$_2$) using EtOAc-hexane 1:9 as eluent, gave 4-allyl-2-fluoro-5-methoxyphenol (5.16 g). $^1$H NMR (CDCl$_3$): δ 6.85 (d, J=11.8 Hz, 1 H), 6.52 (d, J=7.8 Hz, 1 H), 6.0–5.85 (m, 1 H), 5.05 (m, 3 H), 5.00 (m, 1 H), 3.78 (s, 3 H). MS (EI, 70 eV): m/z (rel.int) 182 (M$^+$, 84).

2-Fluoro-5-methoxy-4-propylphenol

4-Allyl-2-fluoro-5-methoxyphenol (5.16 g, 28.3 mmol) was dissolved in EtOH (150 mL) and Pd/C (5%, 250 mg) was added. Hydrogenation for 6 h at room temperature and atmospheric pressure, addition of more Pd/C (5%, 100 mg), continued reaction for 3 h followed by removal of the catalyst and evaporation of the solvent gave 2-fluoro-5-methoxy-4-propylphenol (4.52 g) as an oil. $^1$H NMR (DMSO-d$_6$): δ 9.53 (s, 1 H), 6.85 (d, J=11.8 Hz, 1 H), 6.51 (d, J=7.7 Hz, 1 H), 3.67 (s, 3 H), 2.38 (t, J=7.5 Hz, 2 H), 1.46 (m, J=7.5 Hz, 2 H), 0.84 (t, J =7.4 Hz, 3 H). $^{13}$C MNR (DMSO-d$_6$): δ153.21, 144.84 (d, J=230 HZ), 142.70 (d, J=13 Hz), 120.41 (d, J=5 Hz), 116.46 (d, J=19 Hz), 101.25, 55.62, 30.68, 22.61, 13.71. MS (EI, 70 eV): m/z (rel.int.) 184 (M$^+$, 69).

2-Fluoro-5-methoxy-4-propylphenyl triflate 2-fluoro-5-methoxy-4-propylphenol (4.52 g, 24.5 mmol) was dissolved in CH$_2$Cl$_2$ (100 mL), triethylamine (6.84 mL, 49.1 mmol) and 4-(N,N-dimethylamino)pyridine (5 mg, 0.04 mmol) was added and the solution was cooled to −70° C. Trifluoromethanesulfonic anhydride (6.19 mL, 36.8 mmol) was added dropwise during 20 min and the reaction was kept at −70° C. for another 20 min. CH$_2$Cl$_2$ (100 mL) was added and the solution was washed with water (50 mL) and brine (2×50 mL) followed by drying (MgSO$_4$). Evaporation of the solvent gave 8.2 g of crude product. Filtration through SiO$_2$ (70 g) using CH$_2$Cl$_2$ as eluent and purification by flash chromatography (SiO$_2$, CH$_2$Cl$_2$-hexane 1:2) gave 2-fluoro-5-methoxy-4-propylphenyl triflate (6.08 g) as an oil. $^1$H NMR (DMSO-d$_6$): δ 7.36 (d, J=11.0 Hz, 1 H), 7.21 (d, J=6.4 Hz, 1 H), 3.79 (s, 3 H), 2.52 (t, J=7.7 Hz, 2 H), 1.52 (m, J=7.5 Hz, 2 H), 0.87 (t, J=7.4 Hz, 3 H). $^{13}$C NMR (DMSO-d$_6$): δ 153.62 (d, J=242 Hz), 133.63 (d, J=15 Hz), 132.96 (d, J=6 Hz), 118.15 (q, J=320 Hz), 117.75 (d, J=20 Hz), 106.18, 56.51, 31.00, 21.92, 13.63. MS (EI, 70 eV): m/z (rel.int) 316 (M$^+$, 100).

Methyl 2-fluoro-5-methoxy-4-propylbenzoate

2-Fluoro-5-methoxy-4-propylphenyl triflate (3.00 g, 9.5 mmol), triethylamine (2.91 mL, 20.9 mmol) and methanol (7.0 mL, 173 mmol) were dissolved in DMF (30 mL) and the solution was flushed with CO. 1,3-Bis(diphenylphosphino)propane (151 mg, 0.37 mmol) and palladium-acetate (84 mg, 0.37 mmol) were added and the reaction was stirred at 70° C. and atmospheric pressure for 4.5 h. Evaporation of the solvent and co-evaporation with xylene gave a residue which was extracted between Et$_2$O and 2M NaOH and the organic phase was washed brine, dryed over MgSO$_4$ and evaporated to give 2.3 g of crude product. Purification by flash chromatography (SiO$_2$, CH$_2$Cl$_2$-hexane 1:2) gave methyl 2-fluoro-5-methoxy-4-propylbenzoate (1.46 g) as an oil. $^1$H NMR (DMSO-d$_6$): δ 7.28 (d, J=6.0 Hz, 1 H), 7.12 (d, J=11.4 Hz, 1 H), 3.83 (s, 3 H), 3.80 (s, 3 H), 2.54 (t, J=7.6 Hz, 2 H), 1.53 (m, J=7.6 Hz, 2 H), 0.87 (t, J=7.4 Hz, 3 H). $^{13}$C NMR (DMSO-d$_6$): δ 164.01 (d, J=4 Hz), 155.21 (d, J=251 Hz), 152.95, 138.30 (d, J=8 Hz), 117.93 (d, J=24 Hz), 115.26 (d, J=11 Hz), 111.75, 55.88, 52.20, 31.32, 21.83, 13.66. MS (EI, 70 eV): m/z (rel.int) 226 (M$^+$, 100).

2-Fluoro-5-hydroxy-4-propylbenzoic acid

Methyl 2-fluoro-5-methoxy-4-propylbenzoate (1.27 g, 5.63 mmol) was dissolved in CH$_2$Cl$_2$ (20 mL) and cooled to −70° C. Boron tribromide (1.64 mL, 16.9 mmol) was added and the temperature was slowly raised to 0° C. during 4.5 h. Methylene chloride (20 mL) and 2M NaOH (25 mL) were added and the mixture was stirred over-night at room temperature. Water (20 mL) was added, the phases separated and the aqueous phase was extracted with CH$_2$Cl$_2$ (20 mL) and acidified to pH 1 by concentrated HCl thus precipitating the acid. Ethyl acetate (50 mL) was added to the mixture and the phases separated. The aqueous phase was extracted by additional EtOAc (50 mL) and the combined organic phases were washed with brine (20 mL), dried (MgSO$_4$) and evaporated yielding 2-fluoro-5-hydroxy-4-propylbenzoic acid (1.09 g) Mp: 134.5°–135.5° C. $^1$H NMR (DMSO-d$_6$):

d 12.88 (br, 1 H), 9.57 (br, 1 H), 7.23 (d, J=6.5 Hz, 1 H), 6.96 (d, J=11.6 Hz), 2.48 (t, J=7.5 Hz, 2 H), 1.53 (m, J=7.5 Hz, 2 H), 0.87 (t, J=7.4 HZ, 3 H). $^{13}$C NMR (DMSO-d$_6$): δ 164.96 (d, J=3 Hz), 154.38 (d, J=248 Hz), 150.84 (d, J=2 Hz), 135.82 (d, J=7 Hz), 117.44 (d, J=24 Hz), 116.28 (d, J=11 Hz), 116.22, 31.38, 21.79, 13.65. MS (EI, 70 eV): m/z (rel.int) 198 (M$^+$, 38).

6-Fluoro-3-hydroxy-2-nitro-4-propylbenzoic acid 2-Fluoro-5-hydroxy-4-propylbenzoic acid (500 mg, 2.52 mmol) was dissolved in nitromethane (50 mL) through heating to 40° C. and nitric acid (90%, 120 μL, 2.52 mmol) was added. After 10 min at 40° C. followed by reaction at room temperature for 2 h the solvent was evaporated. The residue was dissolved in EtOAc (150 mL), washed with brine (10 mL), dried (MgSO$_4$) and concentrated to dryness giving 640 mg of crude product. Subsequent purification by flash chromatography (SiO$_2$, EtOAc-HOAc 50:1) afforded pure 6-fluoro-3-hydroxy-2-nitro-4-propylbenzoic acid (294 mg). Mp: 128.0°–129.0° C. $^1$H NMR (DMSO-d$_6$); δ 10.2 (br, 1 H), 7.39 (d, J=10.4 Hz, 1 H), 2.63 (t, J=7.6 Hz, 2 H), 1.55 (m, J=7.5 HZ, 2 H), 0.89 (t, J=7.4 Hz, 3 H). $^{13}$C NMR (DMSO-d$_6$): δ 162.49, 151.66 (d, J=245 Hz), 143.69, 138.74 (d, J=5 Hz), 138.17 (d, J=8 Hz), 120.25 (d, J=23 Hz), 113.82 (d, J=21 Hz), 31.44, 21.92, 13.60. MS (EI, 70 eV): m/z (rel.int) 243 (M$^+$, 88).

6-Fluoro-3-hydroxy-4-propylanthranilic acid hydrochloride

6-Fluoro-3-hydroxy-2-nitro-4-propylbenzoic acid (274 mg, 1.13 mmol) was dissolved in a mixture of dioxane (25 mL) and water (40 mL) and 5% Pd/C (25 mg) was added. Hydrogenation at room temperature and atmospheric pressure for 3 h, addition of more catalyst (10 mg), continued hydrogenation overnight, removal of the catalyst, addition of more dioxane (10 mL) and new catalyst (30 mg) followed by reaction for 3 h, filtration and evaporation of the solvents, gave 205 mg of crude product. Purification by flash chromatography (SiO$_2$, EtOAc-HOAc 50:1) gave 105 mg of an almost pure compound which was dissolved in THF (1.5 mL) and the hydrochloride salt precipitated by addition of HCl/Et$_2$O (3M, 3 ml). The salt was washed with Et$_2$O (3×3 m) and after vacuum-drying 6-fluoro-3-hydroxy-4-propylanthranilic acid hydrochloride (88 mg) was obtained. Mp: 173° C. (dec.). $^1$H NMR (DMSO-d$_6$): δ8.27 (br, 5 H), 6.23 (d, J=12.5 Hz), 2.48 (t, J=7.6 Hz, 2 H), 1.49 (m, J=7.5 Hz, 2 H), 0.86 (t, J=7.3 Hz, 3 H). $^{13}$C NMR (DMSO-d$_6$): δ 167.40, 155.73 (d, J=246 Hz, 139.64 (d, J=4 Hz), 138.11, 133.93 (d, J=10 Hz), 103.91 (d, J=24 Hz), 100.91 (d, J=16 Hz), 31.68, 22.11, 13.82. MS (EI, 70 eV): m/e (rel.int.) 213 (M+, 59).

Example 4 (Method A)

Preparation of 4,6-dichloro-3-hydroxyanthranilic acid 4,6-Dichloro-3-hydroxy-2-nitrobenzoic acid 4,6-Dichloro-3-hydroxybenzoic acid[3] (280 mg, 1.35 mmol) was dissolved in nitromethane (35 mL) by heating to 45° C. Nitric acid (90%, 63 RL,1.35 mmol) was added and after 4 h at 45° C. the solvent was evaporated. The residue was partitioned between EtOAc (100 mL) and water (5 mL), the organic phase washed with brine (5 mL), dried (MgSO$_4$) and evaporated giving 327 mg of crude product. Purification by column chromatography (SiO$_2$) using EtOAc-HOAc 50:1 as eluent afforded pure 4,6-dichloro-3-hydroxy-2-nitrobenzoic acid (232 mg). Mp: 186° C. (dec.). $^1$H NMR (DMSO-d$_6$): δ 7.88 (s, 1 H) $^{13}$C NMR (DMSO-d$_6$): δ163.76, 147.25, 139.03, 133.06, 128.06, 126.28, 118.23. MS (EI, 70 eV): m/z (rel.int) 253/251 (M$^+$, 34/49).

4,6-Dichloro-3-hydroxyanthranilic acid hydrochloride 4,6-Dichloro-3-hydroxy-2-nitrobenzoic acid (223 mg, 0.88 mmol) was dissolved in EtOH (50 mL) and Pd/C (10%, 30 mg) was added. Hydrogenation at atmospheric pressure and at room temperature for 1 h, filtration and evaporation of the solvent gave 205 mg of crude product. Purification by column chromatography (SiO$_2$, EtOAc-HOAc 50:1) gave a residue which was recrystallized from MeOH/water (0.5/1.5 mL). Column chromatography (SiO$_2$, EtOAc-HOAc 400:1) followed by dissolving the free amine in THF (0.6 mL) and precipitating the hydrochloride by adding HCl/Et$_2$O (3M, 1 mL) and Et$_2$O (1 mL) gave 4,6-dichloro-3-hydroxyanthranilic acid hydrochloride (32 mg). Mp: 231° C. (dec.). $^1$H NMR (DMSO-d$_6$): δ 7.0 (br, 5 H), 6.68 (s, 1 H). $^{13}$C NMR (DMSO-d$_6$): δ 167.15, 140.27, 139.05, 122.49, 121.88, 116.24, 113.99. MS (EI, 70 eV): m/z (rel.int.) 223/221 (M$^+$, 42/65).

Example 5 (Method A)

Preparation of 4-Bromo-6-fluoro-3-hydroxyanthranilic acid

6-Fluoro-3-methoxybenzoic acid

4-Fluoro-3-methylanisol (1.0 g, 7.1 mmol) was dissolved in a mixture of pyridine (16 mL) and water (32 mL). Potassium permanganate (3.4 g, 21 mmol) was added and the reaction mixture was refluxed for 3 h and then left at room temperature over night. After filtration and extraction with CH$_2$Cl$_2$ the aqueous phase was acidified with HCl precipitating the product (440 mg).

$^1$ NMR (CD$_3$OD): δ7.44–7.47 (m, 1 H), 7.18–7.16 (m, 2H), 3.86 (s, 3 H); $^{13}$C NMR (CD$_3$OD): δ 167.55, 158.35 (d, J=192 Hz), 156.30, 121.65 (d, J=8.7 Hz), 120.63 (d), 118.94 (d, J=24.4 Hz), 117.03, 56.59.

6-Fluoro-3-hydroxybenzoic acid

6-Fluoro-3-methoxybenzoic acid (500 mg, 2.94 mmol) was mixed with freshly distilled 48% HBr (20 mL) and heated at 100° C. for 14 h. Water and HBr were evaporated and the crude product (462 mg) was used without further purification. $^1$H NMR( CD$_3$OD): δ 7.28–7.29 (m, 1H), 6.92–7.12 (m, 2 H); $^{13}$C NMR (CD$_3$OD): δ 167.80, 157.26 (d, J=249 Hz), 154.77, 122.52 (d, J=10.4 Hz), 120.49 (d, J=11 Hz), 118.77 (d, J=19 Hz), 118.58.

6-Fluoro-3-hydroxy-2-nitrobenzoic acid

6-Fluoro-3-hydroxybenzoic acid (100 mg, 0.64 mmol) was dissolved in CH$_3$NO$_2$ (10 mL) and cooled to 0° C. HNO$_3$ (90%, 31 μL, 0.64 mmol) was added and the reaction was left at 0° C. for 4 h and then at room temperature over night. Evaporation and purification by flash chromatography on SiO$_2$ (Toluene-EtOAc-HOAc) gave the product (22 mg). $^1$H NMR (CD$_3$OD): δ 7.32 (t, J=9.0 Hz, 1 H), 7.15 (dd, J$_1$=9.3 Hz, J$_2$=4.4 Hz, 1 H); $^{13}$C NMR: δ 164.97, 153.68 (d, J=247 Hz), 148.78, 122.67, 122.56, 122.45, 122.13.

4-Bromo-6-fluoro-3-hydroxy-2-nitrobenzoic acid

6-Fluoro-3-hydroxy-2-nitrobenzoic acid (22 mg, 0.11 mmol) was dissolved in acetic acid (2 mL). Sodium acetate (10 mg, 0.12 mmol) and Br$_2$ (10 μL, 0.19 mmol) was added and the reaction mixture was left at room temperature for 14 h. The temperature was raised to 50 and the reaction was continued for another 4 h. Evaporation gave a residue which was dissolved in water, and after adjustment of the pH the aqueous phase was extracted with EtOAc. Washing of the organic phase with water and evaporation gave a crude product which was purified by flash chromatography on SiO$_2$. Eluation with toluene-EtOAc-HOAc afforded the product (23 mg). $^1$ NMR (CD$_3$OD): δ 8.0 (d, J=8.7, 1 H); MS (EI, 70 eV): m/z (rel. int.) 279/281 (M$^+$, 40/38)

4-Bromo-6-fluoro-3-hydroxyanthranilic acid

4-Bromo-6-fluoro-3-hydroxy-2-nitrobenzoic acid (22 mg 0.78 mmol) was dissolved in EtOH (10 mL) and PtS$_2$ (2 mg)

was added. Hydrogenation at room temperature and at atmospheric pressure for 14 h followed by filtration and evaporation gave a crude product. Purification by flash chromatography ( $SiO_2$, toluene-EtOAc-HOAc) afforded the product (4 mg). $^1$H NMR ($CD_3OD$): δ 6.44 (d, J=11.3 Hz, 1 H); MS (EI, 70 eV): m/z (rel. int.) 249/251 ($M^+$, 93/90).

Example 6 (Method B)

Preparation of 4-chloro-3-hydroxy-6-trifluoromethylanthranilic acid

1-Chloro-2-methoxy-3-nitro-5-trifluoromethylbenzene

2-Chloro-6-nitro-4-trifluoromethylphenol[4] (5.3 g, 22 mmol) was dissolved in acetone (120 mL). Potassium carbonate (6.1 g, 44 mmol) and dimethyl sulfate (4.3 mL, 44 mmol) was added and the solution was stirred for 3 h at 80° C. The solvent was evaporated and the crude product was dissolved in EtOAc and extracted with 2M NaOH (2) and brine (2). Drying ($MgSO_4$), filtration and evaporation gave a brown oil (7.9 g) Purification on a silica gel coloumn (EtOAc-toluene-HOAc 100:100:1) gave the title compound as a yellow oil (3.9 g). $^1$H NMR ($CDCl_3$): 7.99 (d, J=2.08 Hz, 1 H), 7.90 (d, J=2.08 Hz, 1 H), 4.09 (s, 3 H). MS (EI, 70 eV): m/z (rel. int.) 257/255 ($M^+$, 17/49).

3-Chloro-2-methoxy-5-trifluoromethylaniline

1-Chloro-2-methoxy-3-nitro-5-trifluoromethylbenzene (3.46 g, 13.5 mmol) was dissolved in MeOH (74 mL). Hydrochloric acid (2M, 13 mL, 26 mmol) and Pd/C (10%, 0.44 g) was added. Hydrogenation at atmospheric pressure and at room temperature for 1 h 30 min, filtration and evaporation of the solvent gave a crude product. Purification by flash chromatography ($SiO_2$, $CH_2Cl_2$-hexarne 1:2 followed by EtOAc-$NH_3$ 100:0.1) yielded the title compound (3.08 g) as an oil. $^1$H NMR ($CDCl_3$): 7.00 (J 1.8 Hz, 1 H), 6.85 (d, J=1.95 Hz, 1 H), 4.11 (br s, 2 H), 3.87 (s, 3 H). MS (EI, 70 eV): m/z (rel. int.) 227/225 ($M^+$, 17/58).

1-Chloro-3-isonitrosoacetamido-2-methoxy-5-trifluoromethylbenzene

Chloral hydrate (334 mg, 2.02 mmol) was dissolved in $H_2O$ (6 mL). A mixture of 3-chloro-2-methoxy-5-trifluoromethylaniline (350 mg, 1.55 mmol) in DMF (2 mL), $H_2O$ (2 mL) and HCl (12M, 0.14 mL, 1.7 mmol) was added. The reaction mixture was stirred at 95° C. for 15 min. Hydroxylamine hydrochloride (431 mg, 6.21 mmol) was added and the stirring at 95° C. for 2 h 40 min was continued. Evaporation and co-evaporation with xylene gave a residue which was extracted between EtOAc and $H_2O$. The $H_2O$ phase was neutralized to pH 7 with $NaHCO_3$ (aq, sat) and then washed with EtOAc (2). The combined organic phases were dried ($Na_2SO_4$), filtered and evaporated. Purification of the crude product (448 mg) by flash chromatography ($SiO_2$, gradient EtOAc-hexane 1:20 1:4) yielded the title compound (146 mg) as a white powder. $^1$H NMR ($CD_3OD$): 8.57 (d, J=1.96 Hz, 1 H), 7.57 (s, 1 H), 7.46 (d, 1 H), 3.94 (s, 3 H). MS (EI, 70 eV): m/z (rel. int.) 298/296 ($M^+$, 18/61).

6-Chloro-7-methoxy-4-trifluoromethylisatin

1-Chloro-3-isonitrosoacetamido-2-methoxy-5-trifluoromethylbenzene (188 mg, 0.63 mmol) was dissolved in $H_2SO_4$ (conc., 4 mL) and stirred at 83° C. for 1 h 15 min. The reaction mixture was poured into ice-water (75 mL). Extraction with EtOAc (250 mL), drying ($Na_2SO_4$), filtration and evaporation gave a crude product (220 mg). Purification by flash chromatography ($SiO_2$, gradient EtOAc-hexane 1:4 4:1) yielded the yellow title compound (13 mg) as a tautomeric mixture according to NMR. $^1$H NMR ($CD_3OD$): 7.41 and 7.35 (2 s, 1 H), 3.95 and 3.90 (2 s, 3 H). MS (EI, 70 eV): m/z (rel. int.) 281/279 ($M^+$, 24/77).

4-Chloro-3-methoxy-6-trifluoromethylanthranilic acid

6-Chloro-7-methoxy-4-trifluoromethylisatin (13 mg, 0.046 mmol) was dissolved in NaOH (0.68M, 0.20 mL, 0.13 mmol) and $H_2O$ (0.20 mL) and then cooled to +7° C. Hydrogen peroxide (30%, 14 L, 0.14 mmol) dissolved in NaOH (0.68M, 0.49 mL, 0.33 mmol) was added dropwise during 1 min. The reaction mixture was stirred for 1 h 15 min at room temperature. Additional $H_2O_2$ (10 L) was added at 7° C. and then stirring was continued at room temperature for 2 h. Acetic acid (54 L, 0.94 mmol) was added, but no precipitation occured. Ethyl acetate (2 mL) was added and pH was raised to 6 with $NaHCO_3$ (aq, sat.). The water phase was washed with EtOAc (3) and the combined organic layers were evaporated and co-evaporated with toluene (2). Purification by flash chromatography ($SiO_2$, gradient EtOAc EtOAc-HOAc 100:1) yielded the title compound (5 mg). $^1$H NMR ($CD_3OD$): 6.98 (s, 1 H), 3.87 (s, 3 H). MS (EI, 70 eV): m/z (rel. int.) 271/269 ($M^+$, 17/48).

4-Chloro-3-hydroxy-6-trifluoromethylanthranilic acid

4-Chloro-3-methoxy-6-trifluoromethylanthranilic acid (5 mg, 0.019 mmol) was dissolved in diethyl ether (1 mL) and HCl (2M, 20 L) was added. The solution was evaporated and co-evaporated with toluene. The residue was dissolved in $CH_2Cl_2$ (2 mL), cooled to −60° C., and $BBr_3$ (9 L, 0.092 mmol) was added followed by stirring at −60° C. for 3 min, 0° C. for 3 h and room temperature for 6 h. Additional $BBr_3$ (4 L, 0.04 mmol) was added at −35° C. and the stirring was continued at room temperature for 2 h. The reaction mixture was cooled to −20 ° C. and added to ice-cold $NaHCO_3$ (2 mL, sat.) followed by stirring for 1 h at room temperature. Methylene chloride (2 mL) was added and pH was adjusted to 5. The phases were separated and the $H_2O$ phase was washed with EtOAc (3). The combined organic layers were dried ($Na_2SO_4$), filtered and evaporated. The crude product was purified on a silica gel coloumn (EtOAc EtOAc-HOAc 100:1) and the title compound was isolated (3 mg). $^1$H NMR ($CD_3OD$): 6.97 (s, 1 H). MS (EI, 70 eV): m/z (rel. int.) 257/255 ($M^+$, 0.16/0.54)

Example 7 (Method E)

Preparation of 4,6-Dibromo-N-4-(2,4-dimethoxyphenyl)butyl-3-hydroxyanthranilic acid 1-(4-bromobutyl)-2,4-dimethoxybenzene Commercially available copper(I)bromide (7.17 g, 50 mmol) and anhydrous lithium bromide (8.68 g, 100 mmol) were added to anhydrous THF (100 mL). Vigorous shaking gave a dark greenish solution. 11.5 mL (5.75 mmol) of this solution was added to a mixture of 1,4-dibromobutane (74.8 g, 346 mmol) in THF (90 mL). The mixture was warmed to 40°C, after which a solution of 2,4-dimethoxyphenylmagnesium bromide (115 mmol) in THF (100 mL), prepared by standard methods, was added over 45 min. The temperature was never more than 50° C. After the addition, the mixture was stirred for an additional 1 h at 50° C. The reaction mixture was allowed to reach 30° C. after which it was poured into ice water (200 mL). Effective stirring for 10 min gave a deep blue color. The mixture was extracted with diethyl ether (2×250 mL), dried ($MgSO_4$) and evaporated. The excess of 1,4-dibromobutane was distilled off, and the residue was filtered through a short column of silica gel (hexane-EtOAC, 95:5). Evaporation gave the title compound as a colorless liquid (23.0 g): $^1$H NMR ($CDCl_3$-d) 7.00 (d, J=8.0 Hz, 1 H), 6.44–6.39 (m, 2 H), 3.79 (s, 6 H), 3.42 (t, J=6.9 Hz, 2 H), 2.56 (t, J=7.5 Hz, 2 H), 1.90–1.83 (m, 2 H), 1.73–1.62 (m, 2 H); $^{13}$C NMR ($CDCl_3$-d) 159.13, 158.24, 129.90, 122.56, 103.74, 98.44, 55.30, 55.22, 33.87, 32.47, 28.56 (two overlapping carbon); MS (EI, 70 eV): m/z (rel.int.) 274/272 ($M^+$, 100/96), 151 (54), 121 (43), 91 (14).

4-(2,4-dimethoxyphenyl)butyraldehyde

A mixture of 1-(4-bromobutyl)-2,4-dimethoxybenzene (11.0 g, 40.2 mmol), sodium hydrogen carbonate (6.75 g, 80.3 mmol) and sodium iodide (9.03 g, 60.2 mmol) in DMSO (80 mL) was stirred at 105° C. for 1.5 h. The reaction mixture was allowed to cool to some extent after which ice water (240 mL) was added. The mixture was extracted with diethyl ether (2×200 mL), washed with brine (50 mL), dried (MgSO$_4$) and concentrated in vacuo. The residue was purified by column chromatography (SiO$_2$, hexane-EtOAc, 80:20) yielding the title compound as a colorless liquid (3.56 g): $^1$H NMR (CDCl$_3$-d) 9.74 (t, J=1.8 Hz, 1 H), 7.00 (d, J=7.9 Hz, 1 H), 6.45–6.40 (m, 2 H), 3.79 (s, 3 H), 3.79 (s, 3 H), 2.59 (t, J=7.4 Hz, 2 H), 2.44–2.39 (m, 2 H), 1.90 (quintet, J=7.4 Hz, 2 H); $^{13}$C NMR (CDCl$_3$-d) 202.91, 159.32, 158.28, 130.14, 121.90, 103.78, 98.44, 55.28, 55.16, 43.25, 28.80, 22.50; MS (EI, 70 eV): m/z (rel.int.) 208 (M$^+$, 31), 164 (44), 151 (100), 121 (76), 91 (16).

4,6-Dibromo-N-4-(2,4-dimethoxyphenyl)butyl-3-hydroxyanthranilic acid

A solution of 4-(2,4-dimethoxyphenyl)butyraldehyde (62 mg, 0.30 mmol) in dry methanol (2 mL) was added to a mixture of 4,6-dibromo-3-hydroxyanthranilic acid (93 mg, 0.30 mmol) and Na$_2$SO$_4$ (128 mg, 0.90 mmol) in methanol (10 mL). The reaction mixture was stirred for 3 h at room temperature. Sodium cyanoborohydride (30 mg, 0.48 mmol) was added, and the mixture was stirred for a further 2 h. Conc. acetic acid (1 mL) was added, and the solvent was evaporated. The residue was partitioned between EtOAc (40 mL) and water (5 mL). The layers were separated, and the aqueous layer was saturated with NaCl (s) and extracted with EtOAc (2×20 mL). The combined organic layers were dried (MgSO$_4$) and evaporated. Recrystallization from EtOAc yielded 24 mg of crystalline product. The mother liquor was purified by column chromatography (SiO$_2$, EtOAc-hexane-conc. HOAc 60:40:1) which gave another 17 mg of product. The combined material was recrystallized from EtOAc-hexane 60:40 (14 mL). The title compound was obtained as white crystals (28 mg). Mp decomposes >150°C.; $^1$H NMR (DMSO-d$_6$) 7.06 (s, 1 H), 6.97 (d, J=8.2 Hz, 1 H), 6.48 (d, J=2.3 Hz, 1 H), 6.40 (dd, J=8.2 Hz, 2.3 Hz, 1 H), 3.73 (s, 1 H), 3.71 (s, 3 H), 3.08 (m, 2 H), 2.43 (m, 2 H), 1.46 (m, 4 H); $^{13}$C NMR (DMSO-d$_6$) 168.29, 158.72, 157.78, 142.66, 138.29, 129.68, 122.93 (two overlapping carbon), 121.91, 111.38, 109.64, 104.26, 98.27, 55.20, 55.01, 44.93, 29.48, 28.53, 26.76; MS (EI, 70 eV): m/z (rel.int.) 505/503/501 (M$^+$, 1/2/1), 461/459/457 (21/42/23), 281/279/277 (26/54/32). Anal.Calcd for C$_{19}$H$_{21}$Br$_2$NO$_5$: C, 45.4; H, 4.2; N, 2.8. Found: C, 45.0; H, 4.1; N, 2.6.

Example 8 (Method E)

Preparation of 4,6-Dibromo-3-hydroxy-N-(2-thienyl)-methylanthranilic acid 4,6-Dibromo-3-hydroxy-N-(2-thienyl)methylanthranilic acid A solution of 2-thiophenecarboxaldehyde (38 mg, 0.34 mmol) in dry methanol (0.8 mL) was added to a mixture of 4,6-dibromo-3-hydroxyanthranilic acid (105 mg, 0.34 mmol) and Na$_2$SO$_4$ (240 mg, 1.7 mmol) in methanol (2 mL). The reaction mixture was stirred overnight at room temperature. Sodium cyanoborohydride (32 mg, 0.51 mmol) was added, and the mixture was stirred for 2 days at room temperature. Conc. acetic acid (1 mL) was added, and the solvent was removed in vacuo. The residue was partitioned between brine and EtOAc (20 mL). The layers were separated and the aqueous layer was extracted with EtOAc (20 mL). The combined organic layers were dried (MgSO$_4$) and concentrated under reduced pressure. The obtained material was purified by column chromatography (SiO$_2$, CH$_2$Cl$_2$-hexane-EtOAc-conc. HOAc 30:30:20:3). Preparative HPLC (H$_2$O-acetonitrile-conc. HOAc 50:50:1) yielded the title compound as a yellowish solid (17 mg): $^1$H NMR (CD$_3$OD-d$_4$) 7.26 (dd, J=5 Hz, 1 Hz), 7.20 (s 1 H), 6.99 (m, 1 H), 6.92 (dd, J=5 Hz, J=5 Hz, 1 H), 4.54 (s, 2 H); MS (TSP): m/z (rel.int.) 410/408/406 (M+1, 5/12/7), 234/232 (31/28), 154 (100).

References

1. Ellis R. C., Whalky W. B, Ball K. J Chem Soc, Perkin Trans 1 (13) 1377–82 (Eng), 1976
2. Sinhababu A. K., Kawase M., Borchardt R. T. Tetrahedron Lett. 28 (36) 4139–42, 1987
3. Chen A. Eur. Pat. Appl. EP 108526 A2 16 May 1984
4. Marhold A., Klauke E., Ger. Offen. DE 2733682, 8 Feb. 1979

Pharmacological method

Materials

[Carboxy-$^{14}$C]3-hydroxyanthranilic acid (6 mCi/mmol) was received from Drs. E. Shaskan and L. Spitznagle (University of Connecticut, Farmington, Conn., U.S.A.). [$^3$H]QUIN was obtained from the Nuclear Research Center (Negev, Israel). All other chemicals and reagents were obtained from commercial suppliers.

Tissue preparations

For routine assays, male Sprague-Dawley rats (150–200 g) were killed by decapitation and their brains rapidly dissected onto ice. Whole forebrains or individual CNS regions were sonicated in four volumes (wt/vol) of distilled water, centrifuged at 50,000 g for 20 min at 4° C., and the resulting supernatant used for the assay. For subcellular fractionation, the method of Mena et al. (1980) was used and the following fractions were collected: P1 (nuclear fraction), P2 (crude synoptosomal fraction), P3 (microsomal fraction), soluble (cytosol fraction), myelin, synaptosomes, and mitochondria. All nonsoluble fractions were sonicated prior to assay.

Measurement of 3-HAO activity

For routine assays, 20 μl of tissue extract (equivalent to 5 mg of original tissue wet weight) were incubated in the presence or absence of inhibitor (in 10 μl) at 37° C. for 30 min in a solution containing 0.3 mM Fe (SO4)2, 38 mM 4-(2-hydroxyethyl)piperazine-1-ethanesulfonic acid (HEPES)/NaOH buffer (pH 6.0), and 5 μM ([14C]3HANA in a total volume of 195 μl. Blank values were obtained under identical conditions using tissue that had been heated for 5 min in a boiling water bath. The incubation was terminated by the addition of 50 μl 6% HClO$_4$, the tubes cooled on ice, and the precipitate removed by a 2-min centrifugation in a Beckman microfuge. 220 μl of supernatant were applied to a Dowex 50 W (200–400 mesh) cation-exchange column (0.5×2 cm), which was washed with 1 ml of distilled H2O to collect the [$^{14}$C] QUIN produced. 5.5 ml of scintillation fluid were added to the eluate and its radioactivity determined by liquid scintillation spectrometry. Preliminary experiments had indicated that 90–95% of [$^{14}$C]QUIN was collected by this procedure, whereas unreacted [$^{14}$C]3HANA remained on the column.

Pharmaceutical formulations

The administration in the novel method of treatment of this invention may conveniently be oral, rectal, or parenteral at a dosage level of, for example, about 1 to 3000 mg/kg, preferably about 10 to 1000 mg/kg and especially about 25 to 250 mg/kg and may be administered on a regimen of 1 to 4 hours per day. The dose will depend on the route of administration, a particularly preferred route being by intravenous infusion of an aqueous solution containing a compound according to formula I. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; or as is suppositories for rectal administration.

To produce pharmaceutical formulations containing a compound according to the present invention in the form of dosage units for oral application, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above-mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

We claim:

1. A compound of the general formula I

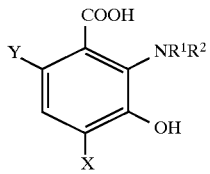

wherein
$R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$
with the proviso that the compound of formula I wherein $R^1$ and $R^2$=H, X=Br and Y=$CH_3$ is excluded;
or a pharmaceutically acceptable salt thereof.

2. A compound according to claim 1 wherein alkyl when $R^1$, $R^2$, X and/or Y represent alkyl; $R^1$ and/or $R^2$ represent arylalkyl; or when X and/or Y represent an alkoxy, alkylthio or fluoralkyl is a straight or branched lower alkyl, preferably a $C_{-C6}$ alkyl.

3. A compound according to claim 1 wherein X and/or Y representing a halogen is selected from iodo, fluoro, chloro and bromo.

4. A compound according to claim 1 wherein aryl when $R^1$ and/or $R^2$ represent aryl or arylalkyl; X and/or Y represent aryloxy or arylthio is a phenyl, furyl or thienyl group in which the ring is optionally further substituted by lower alkyl, lower alkoxy or halogen.

5. A process for the preparation of a compound of formula I according to claim 1 by which comprises
A) in the case where $R^1$ and $R^2$=H; X and Y are the same or different and selected from the group consisting of alkoxy, aryloxy, alkyl, alkylthio, arylthio, fluoroalkyl, halogen, cyano, $OSO_2CH_3$, $OSO_2CF_3$, $OCF_3$ and $SCF_3$ reducing a compound of formula II

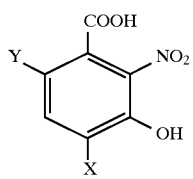

wherein X and Y are as defined in A) above;
B) in the case where $R^1$ and $R^2$ are the same or different and selected from the group consisting of H, alkyl, aryl and arylalkyl; X and Y are the same or different and selected from the group consisting of alkoxy, aryloxy, alkyl, alkylthio, arylthio, fluoroalkyl, halogen, cyano, $OSO_2CH_3$, $OSO_2CF_3$, $OCF_3$ and $SCF_{3k}$ deprotecting a compound of formula III

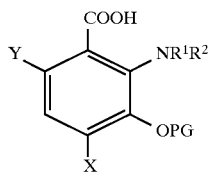

wherein $R^1$, $R^2$, X and Y are as defined in B) above and PG is a protecting group selected from the group consisting of alkyl, benzyl (Bn), 2-(trimethylsilyl)ethoxymethyl (SEM), methoxymethyl (MOM) and 2-methoxyethoxymethyl (MEM);

C) in the case where $R^1$ and $R^2$ are the same or different and selected from the group consisting of H, alkyl, aryl and arylalkyl; X and Y are the same or different and selected from the group consisting of alkoxy, aryloxy, alkyl, alkylthio, arylthio, fluoroalkyl, halogen, cyano, $OSO_2CH_3$, $OSO_2CF_3$, $OCF_3$ and $SCF_3$ deesterifying a compound of formula IV

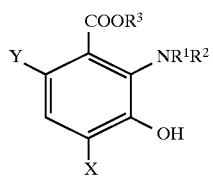   IV wherein $R^1, R^2$, X and Y are as defined in C) above and $R^3$ is selected from the group consisting of alkyl, Bn, SEM, MEM, MOM and 2,2,2-trichloroethyl;

D) in the case where $R^1$ and $R^2$ are the same or different and selected from the group consisting of H, alkyl, aryl and arylalkyl; X and Y are the same or different and selected from the group consisting of alkoxy, aryloxy, alkyl, alkylthio, arylthio, fluoroalkyl, halogen, cyano, $OSO_2CH_3$, $OSO_2CF_3$, $OCF_3$ and $SCF_3$ deesterifying and deprotecting a compound of formula V

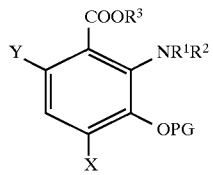   V wherein $R^1$, $R^2$, X and Y are as defined in D) above and $R^3$ and PG are selected from the group consisting of alkyl, Bn, SEM, MEM and MOM; or E) in the case where $R^1$ alkyl, aryl or arylalkyl; $R^2$=H, alkyl, aryl or arylalkyl; X and Y are the same or different and selected from the group consisting of alkoxy, aryloxy, alkyl, alkylthio, arylthio, fluoroalkyl, halogen, cyano, $OSO_2CH_3$, $OSO_2CF_3$, $OCF_3$ and $SCF_3$ alkylating a compound of formula VI

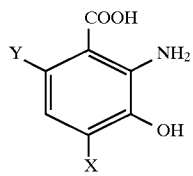   VI wherein X and Y are as defined in E) above.

6. A pharmaceutical formulation containing a compound of the general formula I

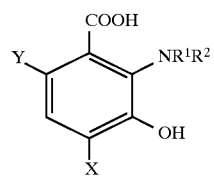   I wherein
  $R^1$ and $R^2$ are the same or different and selected from H, alkyl, aryl and arylalkyl;
  X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$;
as active ingredient and a pharmaceutically acceptable carrier.

7. A method for the prevention or treatment of neurodegeneration which comprises administering to a host in need of such a treatment a sufficient amount of a compound of formula I

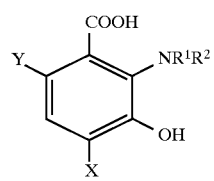   I or a pharmaceutically acceptable salt thereof wherein
  $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$.

8. A compound of the general formula III

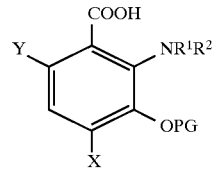   III wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ and PG is a protecting group selected from the group consisting of alkyl, Bn, SEM, MEM or MOM with the two provisos that compounds of formula III wherein $R^1$ and $R^2$=H, X=$OCH_3$, Y=Br, Cl or $OCH_3$ and PG=$CH_3$, and wherein $R^1$ and $R^2$=H, X and Y=$CH_3$ and PG=$CH_3$ are excluded.

9. A compound of the general formula IV

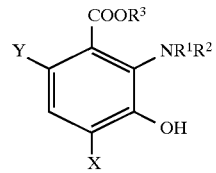   IV wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; and $R^3$ is selected from alkyl, Bn, SEM, MEM, MOM and 2,2,2-trichloroethyl.

10. A compound of the general formula V

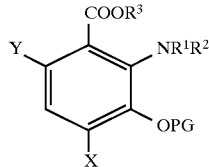
V wherein $R^1$ and $R^2$ are the same or different and selected from H, alkyl, aryl and arylalkyl; X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$; $R^3$ and PG are selected from alkyl, Bn, SEM, MEM and MOM with the proviso that compound of formula V wherein $R^1$ and $R^2$=H, X=$OCH_3$, Y=Cl, PG and $R^3$=$CH_3$ is excluded.

11. A compound of the general formula VI

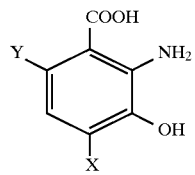
VI wherein X and Y are the same or different and selected from alkoxy, aryloxy, alkyl, alkylthio, arylthio, fluoroalkyl, halogen, cyano, $OSO_2CH_3$, $OSO_2CF_3$, $OCF_3$ and $SCF_3$ with the proviso that compound of formula VI wherein X=Br and Y=$CH_3$ is excluded.

* * * * *

UNITED STATES PATENT AND TRADEMARK OFFICE
CERTIFICATE OF CORRECTION

PATENT NO. : 5,883,129
DATED : March 16, 1999
INVENTOR(S) : Björk et al.

It is certified that error appears in the above-identified patent and that said Letters Patent is hereby corrected as shown below:

Col. 24, line 24 (claim 2, line 5), change "$C-c_6$" to -- $C_1-C_6$ --;

Col. 24, line 35 (claim 5, line 2), delete "by";

Col. 24, line 56 (claim 5, line 15), change "$SCF_{3k}$" to -- $SCF_3$ --;

Col. 25, line 47 (claim 5), after "$R^1$", insert -- = --; and

Col. 26, line 18 (claim 7, line 1), delete "prevention or".

Signed and Sealed this

Ninth Day of November, 1999

Q. TODD DICKINSON

Attest:

Attesting Officer

Acting Commissioner of Patents and Trademarks